(12) United States Patent
Bock-Aronson et al.

(10) Patent No.: US 11,400,245 B2
(45) Date of Patent: Aug. 2, 2022

(54) RESPIRATOR MASK

(71) Applicant: Breathe99 LLC, Minneapolis, MN (US)

(72) Inventors: Max Bock-Aronson, Minneapolis, MN (US); Coleman Rollins, Chicago, IL (US); Jorge Alberto Treviño Blanco, Minneapolis, MN (US); Joél Valdez, Minneapolis, MN (US)

(73) Assignee: Breathe 99 Corporation, Minneapolis, MN (US)

( * ) Notice: Subject to any disclaimer, the term of this patent is extended or adjusted under 35 U.S.C. 154(b) by 270 days.

(21) Appl. No.: 16/596,735

(22) Filed: Oct. 8, 2019

(65) Prior Publication Data

US 2020/0108218 A1 Apr. 9, 2020

Related U.S. Application Data

(60) Provisional application No. 62/742,882, filed on Oct. 8, 2018.

(51) Int. Cl.
*A61M 16/06* (2006.01)
*A61M 16/10* (2006.01)
*A61M 16/20* (2006.01)

(52) U.S. Cl.
CPC .......... *A61M 16/06* (2013.01); *A61M 16/107* (2014.02); *A61M 16/1065* (2014.02); *A61M 16/209* (2014.02)

(58) Field of Classification Search
CPC ....... A62B 18/02; A62B 18/10; A62B 18/025; A62B 9/02; A62B 9/04; A62B 7/10
See application file for complete search history.

(56) References Cited

U.S. PATENT DOCUMENTS

| | | | | |
|---|---|---|---|---|
| 3,467,093 A * | 9/1969 | Hotz | ...................... | A62B 18/02 128/206.24 |
| 3,519,012 A * | 7/1970 | Patten | .................... | A62B 18/10 137/102 |
| 4,630,604 A * | 12/1986 | Montesi | ............... | A62B 18/025 128/206.15 |
| 6,921,417 B2 * | 7/2005 | Persson | ..................... | A61F 2/20 623/9 |
| 2012/0103339 A1 * | 5/2012 | Koehler | ................. | A62B 18/02 128/206.14 |
| 2016/0001104 A1 * | 1/2016 | Lewin | ..................... | F16K 31/12 128/205.24 |
| 2019/0001187 A1 * | 1/2019 | Costella | ............ | A61M 16/0006 |
| 2019/0009114 A1 * | 1/2019 | Han | ........................ | A62B 9/00 |
| 2019/0358473 A1 * | 11/2019 | Szasz | .................. | G08B 21/182 |

* cited by examiner

*Primary Examiner* — Margaret M Luarca
*Assistant Examiner* — Cana A Gallegos
(74) *Attorney, Agent, or Firm* — Todd R. Fronek; Larkin Hoffman Daly & Lindgren, Ltd

(57) ABSTRACT

A respirator mask includes a facepiece configured to create a seal with a face of a user and a mask frame coupled with the facepiece. A port assembly is coupled with the mask frame and an inhalation path including a filter, a first valve seat and a first valve member, the filter and first valve member coupled with the first valve seat on opposed sides. An exhalation path includes a second valve seat and a second valve member, the second valve member surrounding the first valve seat.

5 Claims, 12 Drawing Sheets

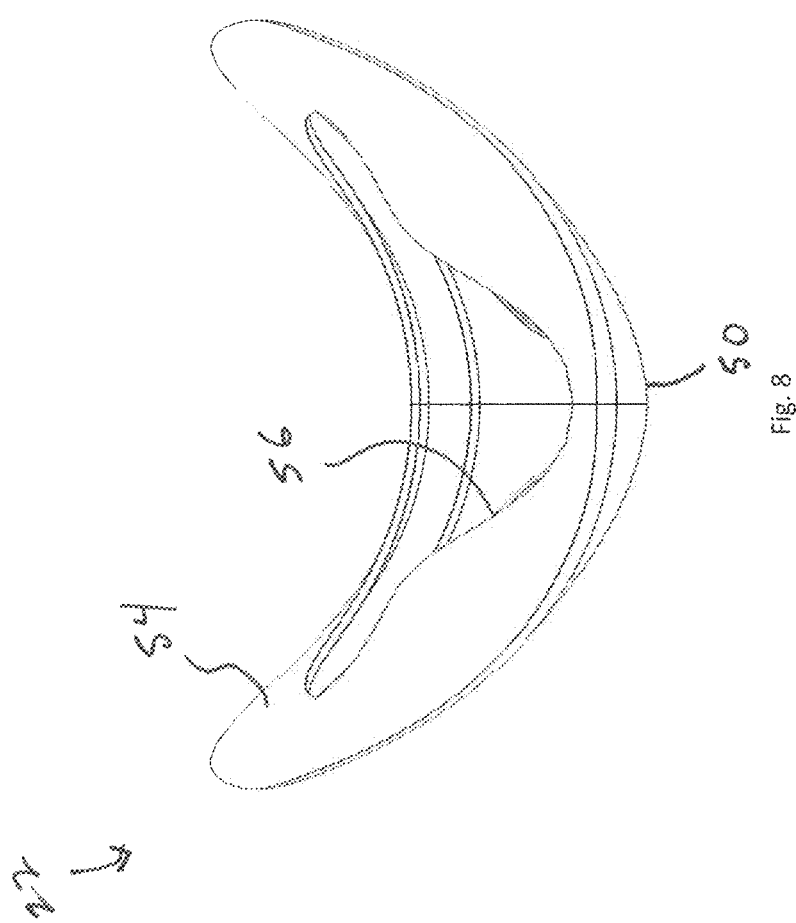

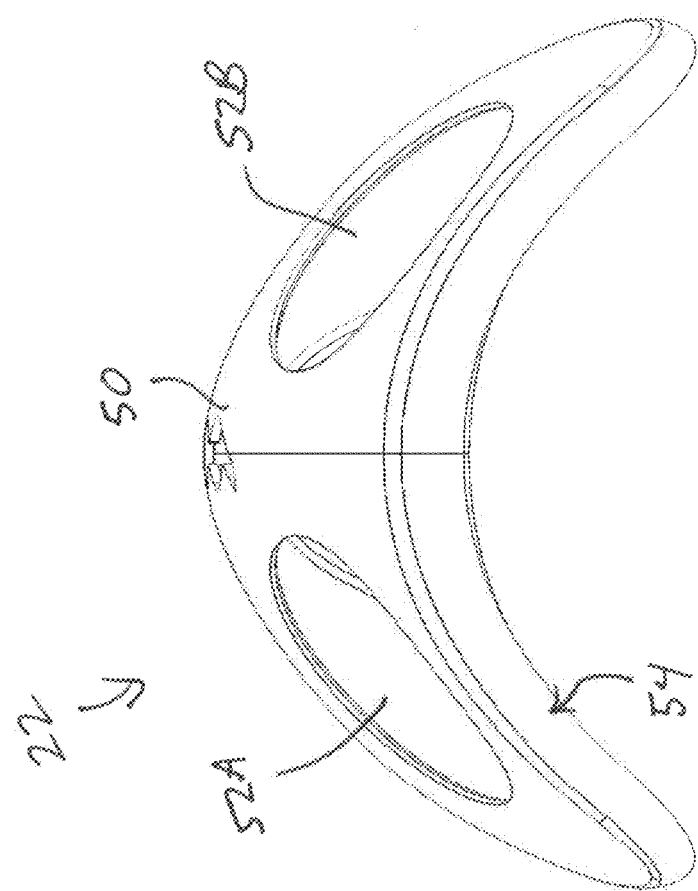

RESPIRATOR MASK

BACKGROUND

Outdoor air pollution is becoming an increasingly severe environmental health risk. People who are exposed to common outdoor pollutants including ozone, particulate matter, and nitrogen dioxide experience an increased risk of developing chronic respiratory diseases, ischemic heart attack, and stroke. Those who have decreased lung function such as children and seniors experience even higher rates of air pollution related morbidities.

There are numerous types of reusable respirators worn by people in work environments with contaminated air. While these respirators can be effective at filtering airborne pollutants, they can be large, heavy, and unattractive. As such, these devices are generally overly cumbersome for everyday protection, forcing the general public to find alternative options.

There are three general types of respiratory protection worn by the general public: low protection cloth and paper masks, filtering facemasks, and reusable cloth masks with replaceable filters. Low protection cloth and paper masks are effective at reducing the spread of germs, however are not designed to filter small pollutants that can be harmful to lung health. Filtering facemasks are effective at filtering most harmful pollutants; however, they are intended for use in industrial settings and as such, are neither aesthetic, adjustable, or customizable. Reusable cloth masks with replaceable filters offer good protection and are designed for use by the general public. A drawback of these masks is that they don't provide a seal around the nose and mouth which results in two issues: (1) buildup of condensation that creates fogging of glasses, and (2) large, expensive filters. To reduce costs, many wearers of reusable fabric masks use the disposable filters much longer than their recommended efficient filter life, which reduces the efficacy of the mask and exposes the user to harmful air.

SUMMARY

A respirator mask includes a facepiece configured to create a seal with a face of a user and a mask frame coupled with the facepiece. A port assembly is coupled with the mask frame and an inhalation path including a filter, a first valve seat and a first valve member, the filter and first valve member coupled with the first valve seat on opposed sides. An exhalation path includes a second valve seat and a second valve member, the second valve member surrounding the first valve seat.

BRIEF DESCRIPTION OF THE DRAWINGS

FIG. 8 is a top view of the facepiece of FIG. 7.
FIG. 9 is a bottom view of the facepiece of FIG. 8.

DESCRIPTION

Figure 1:
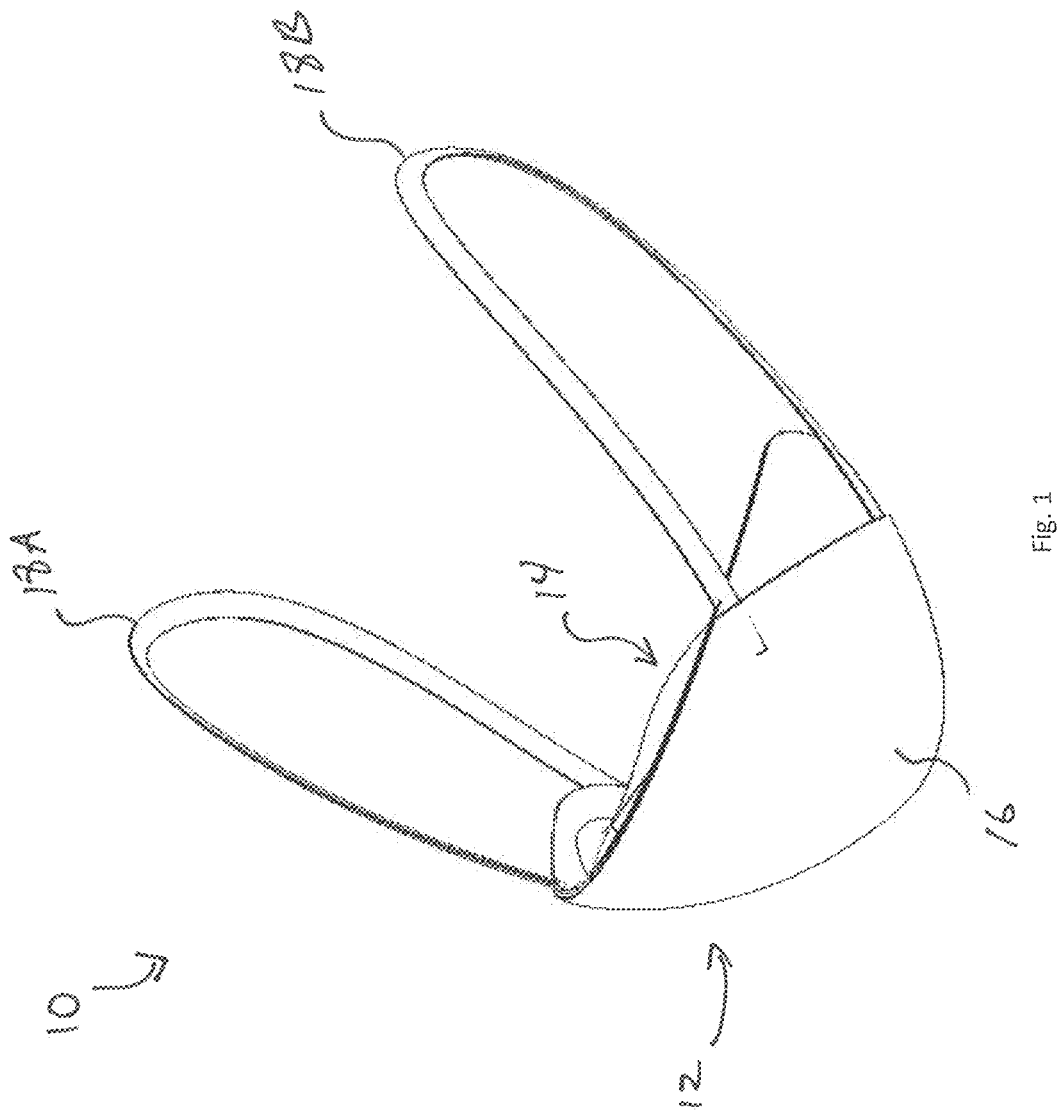
FIG. 1 is a perspective view of a respirator mask.
Figure 2:
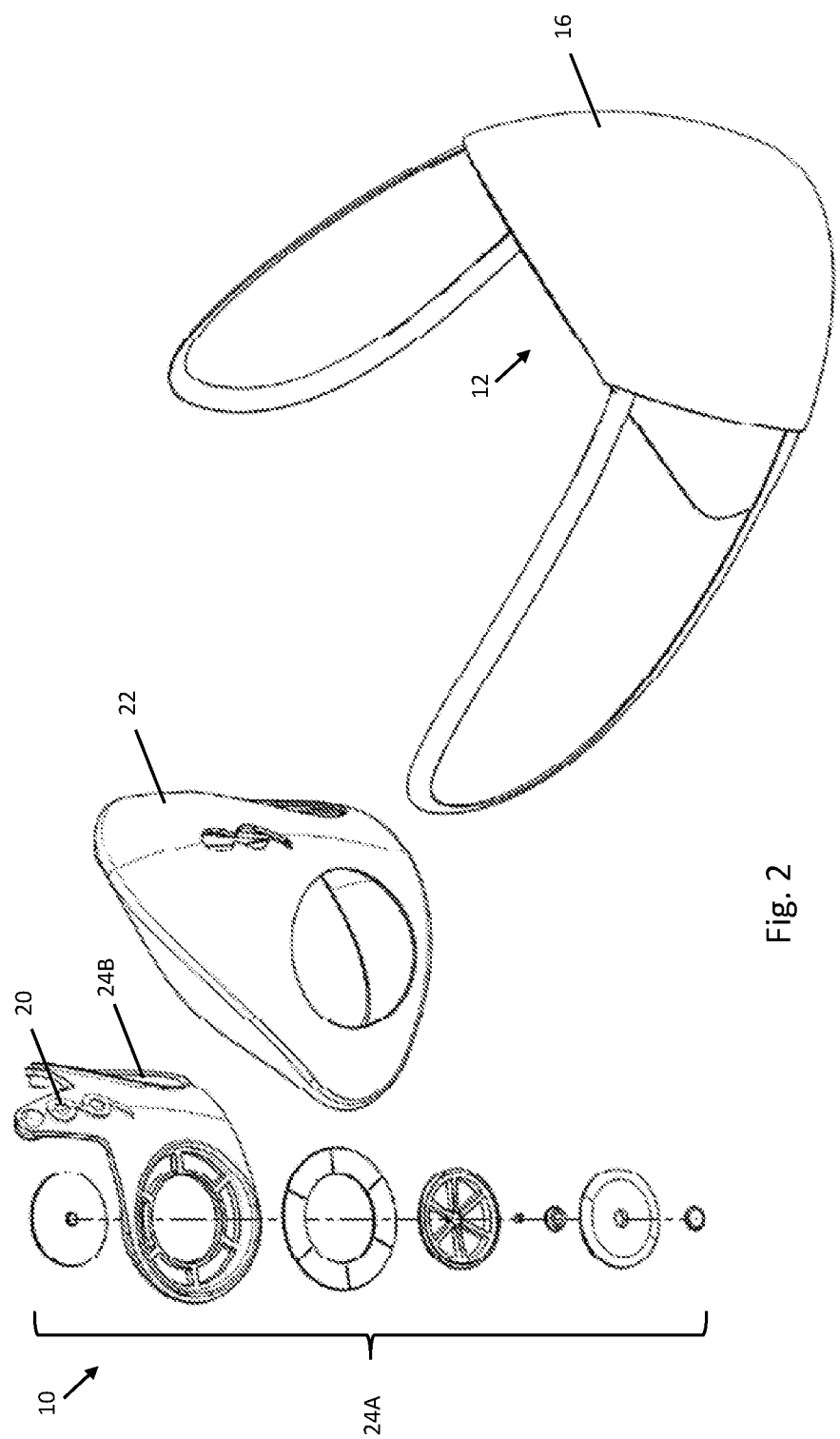
FIG. 2 is a front partially exploded perspective view of the respirator mask of FIG. 1.

As illustrated in FIGS. 1 and 2, a respirator mask 10 includes head gear 12 and a mask assembly 14. The head gear 12 includes a main fabric body 16 and that is connected with opposed straps or cords 18a and 18b. In one embodiment, the fabric body 16 includes a thin, semi-rigid plastic lining that provides structural integrity. Additionally, the fabric body 16 can include a connection mechanism (e.g., loops, buttons, magnets) to connect the fabric body 16 to the mask assembly 14. The fabric body 16 can be comprised of different textile materials as desired. In one embodiment, multiple materials of the fabric body 16 are attached using sewing and other bonding techniques such as radiofrequency or ultrasonic welding. Example textile materials include one or more of Lycra™, Tencel™, polyester, polypropylene, cotton, X-Static™ and/or combinations thereof. In one example, the material for fabric body 16 is selected to exhibit breathability as well as include moisture and odor-reducing properties. Straps 18 loop behind a user's ears to provide retention for the mask assembly 14 against a user's face. In addition, straps 18 can be adjusted either manually using a standard buckle or automatically using a self-adjusting system.

Figure 3:
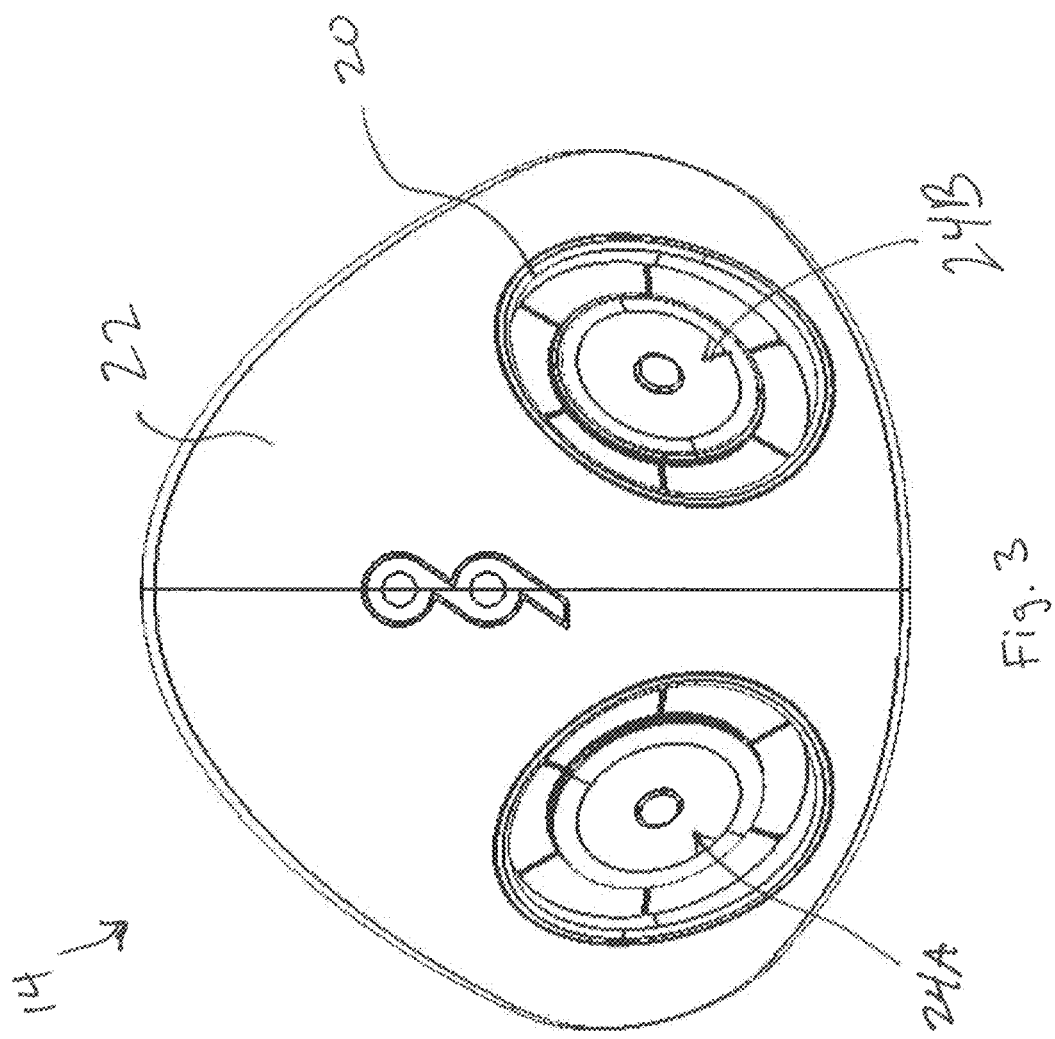
FIG. 3 is a front perspective view of a mask assembly.
Figure 4:
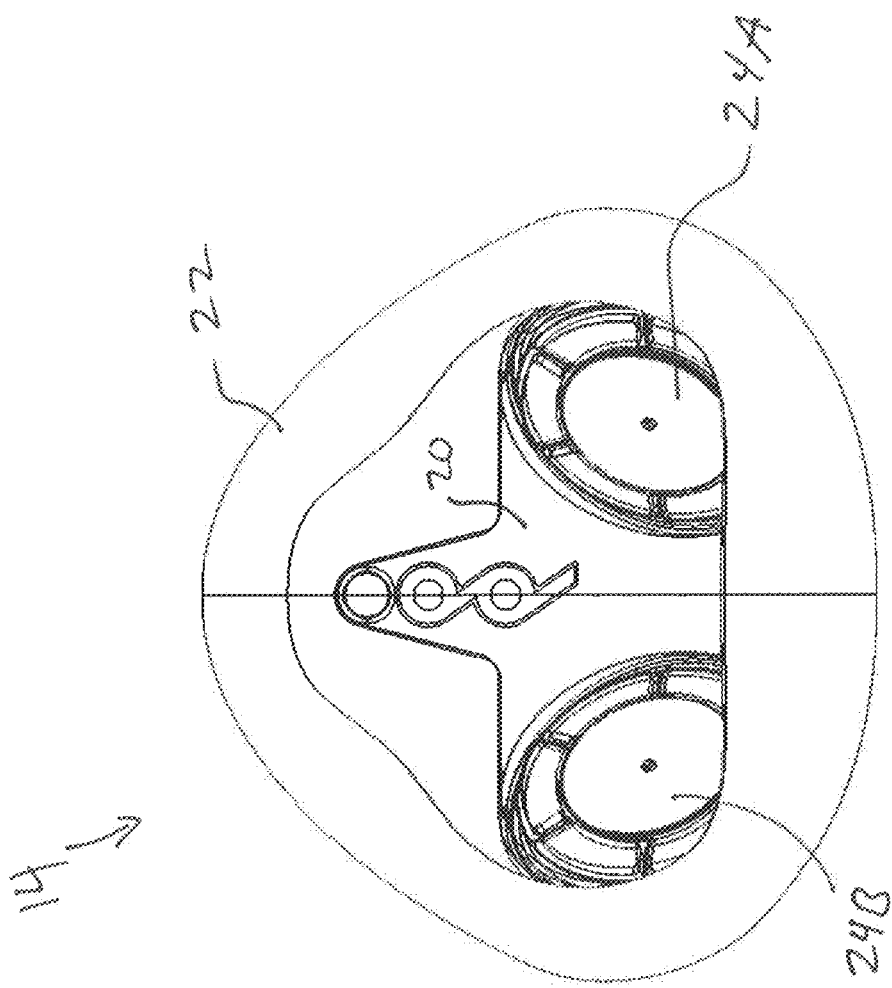
FIG. 4 is a rear perspective view of the mask assembly of FIG. 3.

With further reference to FIGS. 3 and 4, the mask assembly 14 includes a mask frame 20, a facepiece 22 and first and second port assemblies 24a and 24b. Mask frame 20, in one embodiment, is formed of a semi-rigid plastic material to provide structure to the facepiece 22 and support the port assemblies 24. Facepiece 22 is formed of a compliant material (e.g., silicone) that can be molded over mask frame 20, for example using a two-shot or an insert molding manufacturing technique. Port assemblies 24 each include an inhalation valve and exhalation valve. In one embodiment, the inhalation valve and exhalation valve are coaxially arranged, with a port for one of the valves surrounding the port for the other valve, as discussed below. When worn on the face, these valves work in conjunction to create an interior air cavity or chamber that is separate from ambient air. In particular, each port assembly establishes an inhalation path, which directs ambient air from outside the mask 10 toward a user's mouth, and an exhalation path, which directs exhaled air from the user's mouth outside the mask 10.

Figure 5:
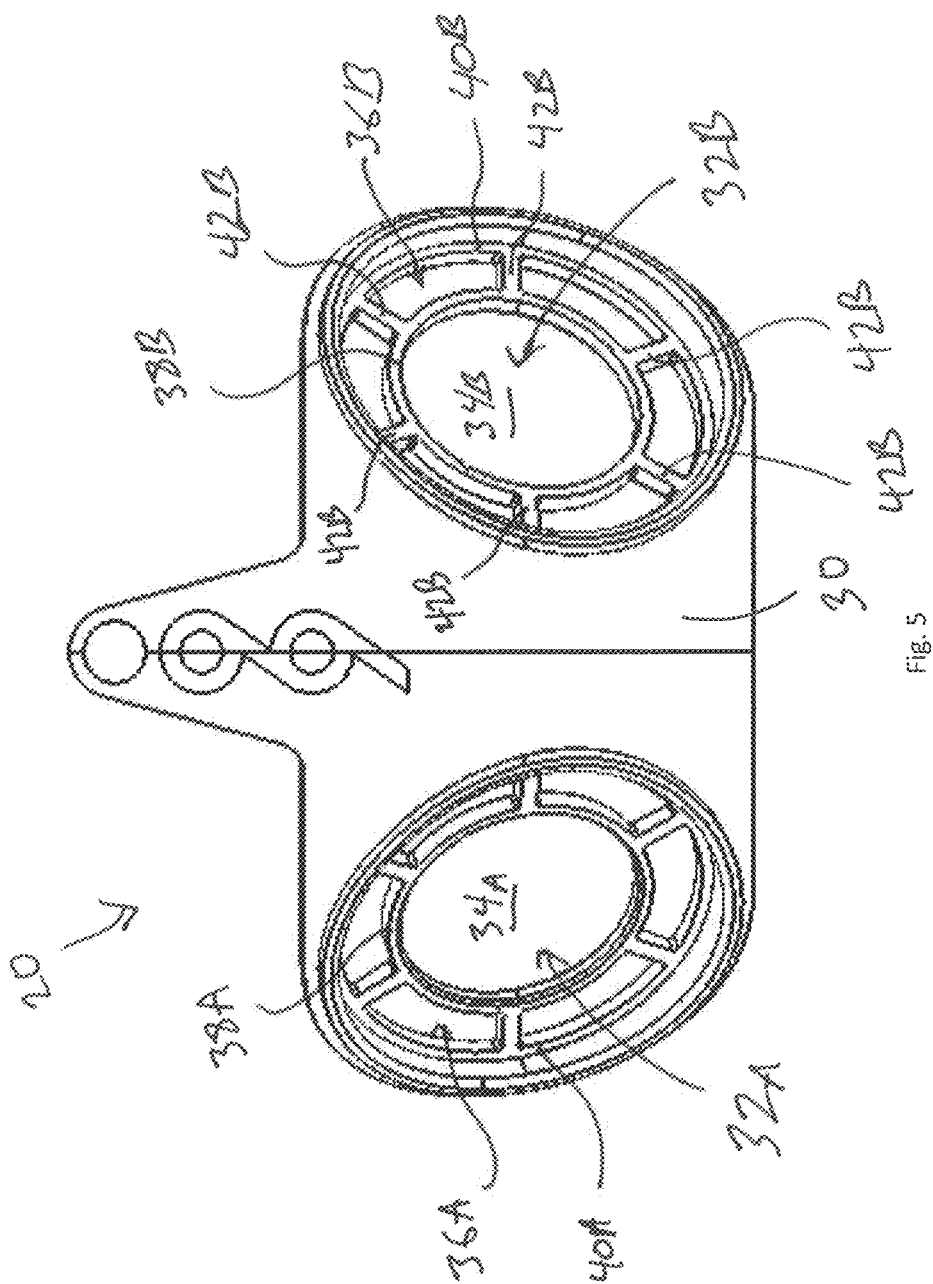
FIG. 5 is a front perspective view of a mask frame.
Figure 6:
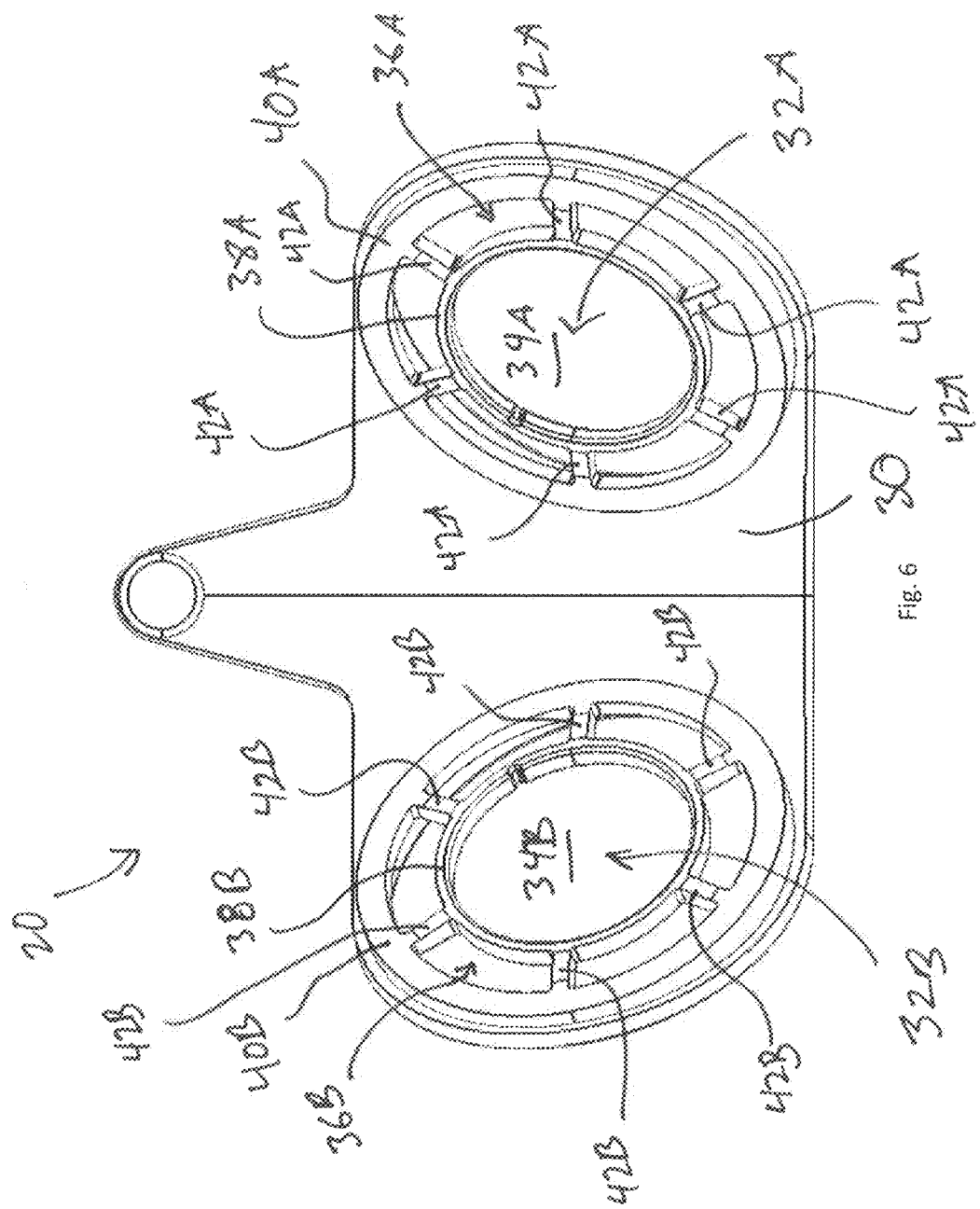
FIG. 6 is a rear perspective view of the mask frame of FIG. 5.

With further reference to FIGS. 5 and 6, the mask frame 20 includes a central mask body 30 defining first and second port openings 32a and 32b. Each of the port openings 32 include a corresponding central opening 34 and an annular opening 36 surrounding the central opening 34. The central opening 34 is formed by a central ring 38 that is supported and spaced apart from a corresponding annular rim 40 coupled with the central mask body and supported by one or more radially extending support structures 42, herein embodied as spokes. In the embodiment illustrated, the central openings 34 serve as inhalation ports for the respiratory mask 10, wherein air flow caused by inhalation of the user is forced through openings 34. In addition, the annular openings 36 form an exhalation port for the respiratory mask 10, wherein air flow caused by exhalation of the user is forced through the openings 36 (i.e., the space between ring 38 and rim 40, as limited by structures 42).

Figure 7:
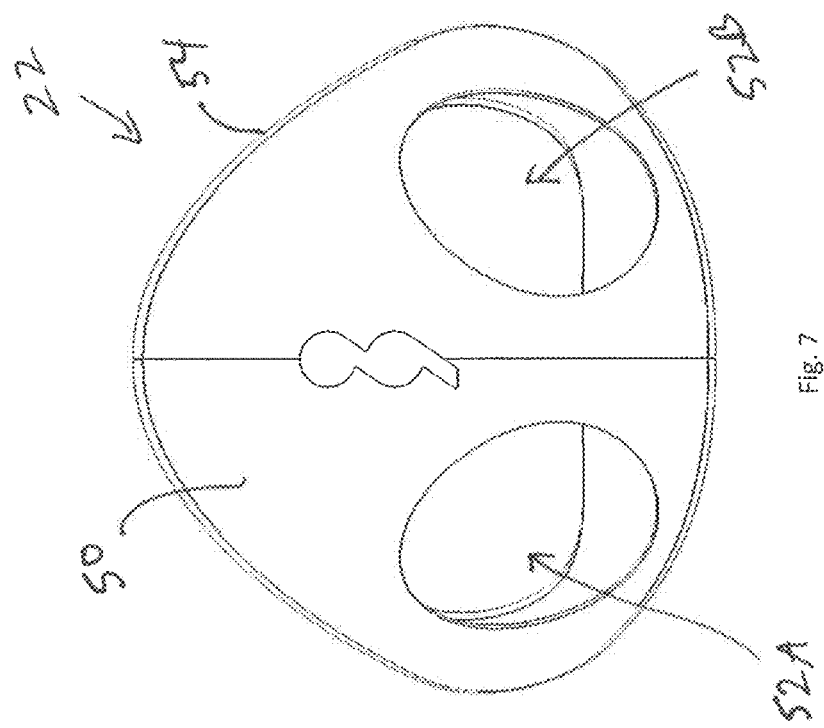
FIG. 7 is a front perspective view of a facepiece.
Figure 11:
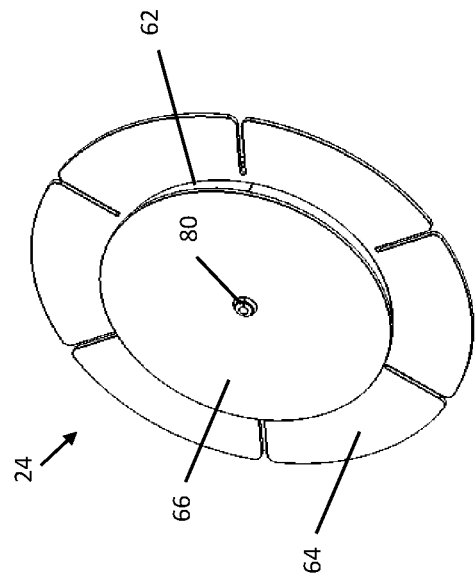
FIG. 11 is a rear perspective view of the port assembly of FIG. 10.
Figure 10:
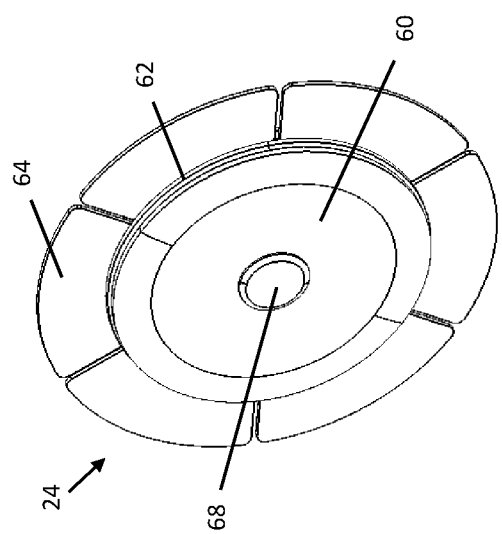
FIG. 10 is a front perspective view of a port assembly.
Figure 12:
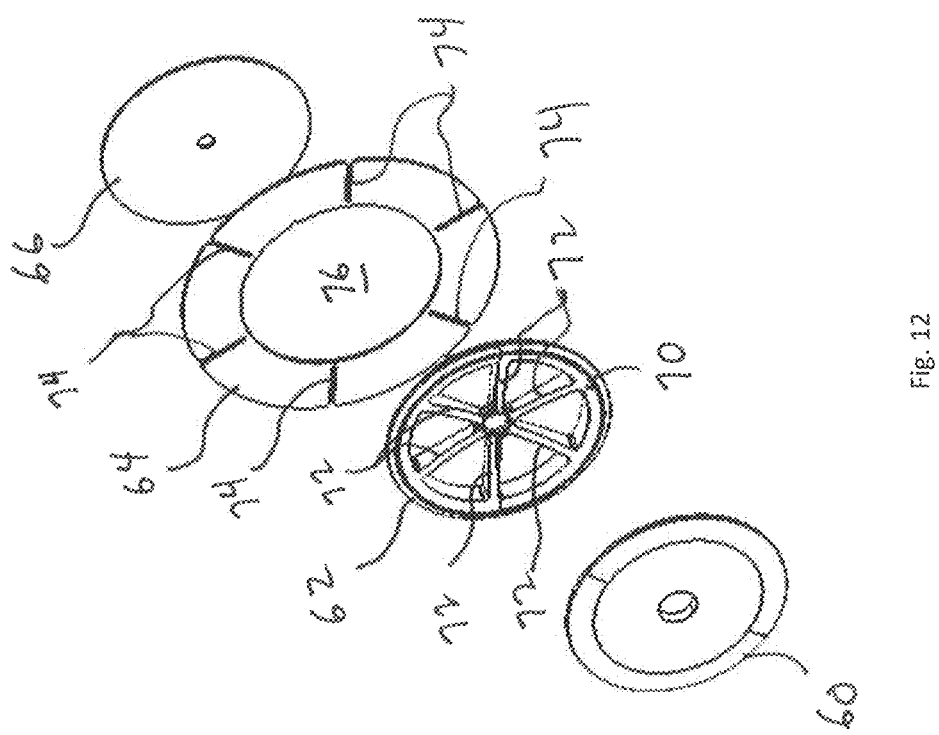
FIG. 12 is a front exploded view of the port assembly of FIG. 10.
Figure 13:
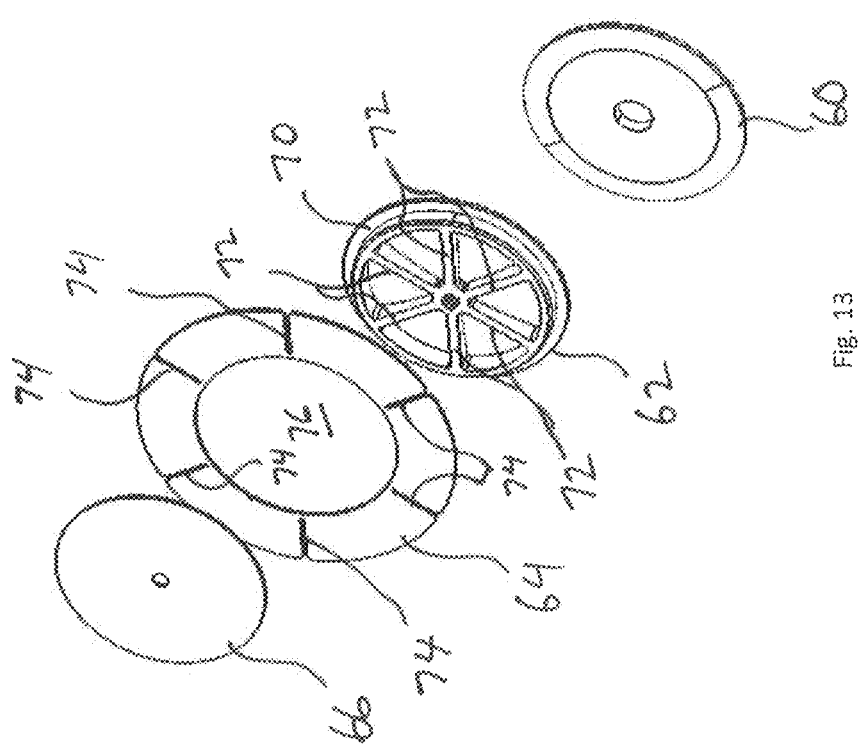
FIG. 13 is a rear exploded view of the port assembly of FIG. 10.

With reference to FIGS. 7-9, the facepiece 22 includes a main body 50 defining ports 52 and an annular cushion 54 configured to create a seal with a user's face. In one embodiment, the annular cushion 54 is formed of a compliant material (e.g., a thermoplastic urethane, a thermoplastic elastomer or silicone resin) whose geometry is matched to the physiology of the human face to create an airtight seal around a user's nose and mouth. A region 56 of cushion 54 that conforms to the nose is designed to sit lower on the nose to such that mask 10 can accommodate the use of eye glasses by a user wearing the mask 10. The region 56 rests approximately midway along the user's nose bridge.

With reference to FIGS. 10-13, port assembly 24 includes a filter 60, a valve seat 62, a first valve member 64 and a second valve member 66. Together, these components are axially aligned (see, e.g., FIG. 2 showing an axis), with the filter 60, valve seat 62 and valve member 66 receiving air flow upon inhalation of a user and the valve member 64 receiving air flow upon exhalation of the user.

In the illustrated embodiment, filter 60 is circular in shape and can include one or multiple layers of filter media such as, but not limited to woven polypropylene and activated carbon. Filter 60 can be secured to valve seat 62 using a suitable attachment mechanism 68. The attachment mechanism 68 can take various forms. In one example, the attachment mechanism 68 can be attached to the seat 62 through a mechanical connection such as a press or interference fit. In another embodiment, the attachment mechanism 68 can be magnetic wherein a first magnet is adhered to the seat 62 and a second magnet is adhered to the filter 60 (see, e.g., FIG. 2 for magnetic components). Regardless of the various form of attachment mechanism 68, filter 60 is secured to the seat 62 and axially aligned with the seat 62 using the attachment mechanism 68.

Upon assembly, the filter 60 is configured to be positioned within the valve seat 62. In one embodiment, the valve seat 62 is cup or dish shaped such that its front surface forms a curved portion to receive the filter 60. As a result, the filter 60 can slightly deflect when connected to the seat 62. In addition to having a cup-shaped front surface 62, the valve seat 62 is formed of an annular ring 70 and a plurality of spokes 72 extending inwardly from the annular ring 70.

The first valve member 64 can be formed of a membrane that is seated against the outer annular ring 40 and inner annular ring 38 of the mask frame 20. In one example, valve seat 62 can secure valve member 64 against annular ring 38. As illustrated, the valve member 64 is formed of a membrane having radial relief cuts 74 and a central opening 76. When mask 10 is assembled, the central opening 76 surrounds the valve seat 62 and the relief cuts 74 are aligned with respective support structures 42 of the mask frame 30. Upon exhalation from a user, air exits through openings 36 such that the valve member 64 deflects and allows exhaled air to pass through the port assembly 24. Accordingly, the valve member 64 is oriented or biased against the mask frame 20 until the presence of a positive pressure gradient between air cavity within the facepiece 22 and ambient air as a result of user exhalation.

Additionally, the second valve member 66 can form a membrane that seats against a back surface of the valve seat 62. The valve member 66 can be formed of a circular membrane connected mechanically to the valve seat 62 with a suitable attachment mechanism 80. Valve member 66 is oriented or biased against the valve seat 62 such that it prevents airflow into the interior air chamber of the respirator mask 10 until the presence of a negative pressure gradient between the mask's interior air chamber and the ambient air as a result of user inhalation. Upon inhalation, the valve member 66 deflects, allowing air to flow through filter and through the valve seat 62 to a user's mouth.

Various embodiments of the invention have been described above for purposes of illustrating the details thereof and to enable one of ordinary skill in the art to make and use the invention. The details and features of the disclosed embodiment[s] are not intended to be limiting, as many variations and modifications will be readily apparent to those of skill in the art. Accordingly, the scope of the present disclosure is intended to be interpreted broadly and to include all variations and modifications coming within the scope and spirit of the appended claims and their legal equivalents.

The invention claimed is:

1. A respirator mask, comprising:
  a facepiece configured to create a seal with a face of a user, the facepiece creating an interior chamber separate from ambient air;
  a mask frame molded with the facepiece and including first and second port assemblies positioned in the facepiece, each of the first and second port assemblies comprising:
    an annular ring including a first side facing the interior chamber and a second side opposite the first side facing ambient air, the annular ring defining a central opening, the annular ring including a plurality of support structures extending into the central opening;
    a circular filter positioned against the plurality of support structures on the second side of the annular ring; and
    an attachment mechanism facing the second side of the annular ring and configured to attach the filter to the plurality of support structures; and
  wherein the first port assembly includes:
    an inhalation path including a first valve member and the circular filter of the first port assembly, the first valve member coupled with the annular ring of the first port assembly on opposed sides of the mask frame; and
    an exhalation path including a second valve member, the second valve member surrounding the annular ring of the first port assembly, wherein the second valve member includes radial relief cuts; and
  a fabric body positioned around the facepiece and configured to secure the facepiece to the face of the user.

2. The respirator mask of claim 1, wherein each circular filter is coupled with the corresponding annular ring using a magnetic connection mechanism.

3. The respirator mask of claim 1, wherein the second port assembly includes:
  a second inhalation path including a third valve member, the circular filter of the second port assembly and third valve member coupled with the annular ring of the second port assembly on opposed sides; and
  a second exhalation path including a fourth valve member, the fourth valve member surrounding the annular ring of the second port assembly.

4. The respirator mask of claim 1, wherein the first valve member is substantially circular and the second valve member is substantially annular, the first valve member and second valve member sharing a central axis.

5. The respirator mask of claim 1, wherein the mask frame defines a central mask body having first and second openings on opposed sides of the central mask body, the first and second port assemblies positioned in the first and second openings, respectively.

* * * * *